US 6,926,662 B1
(12) United States Patent
Aboul-Hosn et al.

(10) Patent No.: US 6,926,662 B1
(45) Date of Patent: Aug. 9, 2005

(54) LEFT AND RIGHT SIDE HEART SUPPORT

(75) Inventors: Walid N. Aboul-Hosn, Fair Oaks, CA (US); William R. Kanz, Sacramento, CA (US); Jodi Akin, Alamo, CA (US); Michael Guidera, Carmichael, CA (US); Robert G. Matheny, Carmel, IN (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

(21) Appl. No.: 09/868,973

(22) PCT Filed: Dec. 23, 1999

(86) PCT No.: PCT/US99/30816

§ 371 (c)(1),
(2), (4) Date: Aug. 20, 2001

(87) PCT Pub. No.: WO00/37139

PCT Pub. Date: Jun. 29, 2000

Related U.S. Application Data

(60) Provisional application No. 60/113,771, filed on Dec. 23, 1998.

(51) Int. Cl.[7] .................................................. A61M 1/10
(52) U.S. Cl. .......................................... 600/16; 623/3.1
(58) Field of Search ...................... 600/16, 17; 623/3.1, 623/11.1, 904, 910, 913, 922, 3.26, 3.3

(56) References Cited

U.S. PATENT DOCUMENTS

| | | | |
|---|---|---|---|
| 3,995,617 A | | 12/1976 | Watkins et al. |
| 4,129,129 A | | 12/1978 | Amrine |
| 4,655,745 A | | 4/1987 | Corbett |
| 4,955,856 A | | 9/1990 | Phillips |
| 5,738,649 A | * | 4/1998 | Macoviak ..................... 604/43 |
| 5,741,234 A | | 4/1998 | Aboul-Hosn |
| 5,868,702 A | * | 2/1999 | Stevens et al. .......... 604/96.01 |
| 6,086,570 A | | 7/2000 | Aboul-Hosn et al. |
| 6,113,536 A | | 9/2000 | Aboul-Hosn et al. |
| 6,123,725 A | | 9/2000 | Aboul-Hosn |
| 6,152,704 A | | 11/2000 | Aboul-Hosn et al. |
| 6,210,133 B1 | | 4/2001 | Aboul-Hosn et al. |
| 6,210,397 B1 | | 4/2001 | Aboul-Hosn et al. |
| 6,234,960 B1 | | 5/2001 | Aboul-Hosn et al. |
| 6,287,319 B1 | | 9/2001 | Aboul-Hosn et al. |
| 6,295,877 B1 | | 10/2001 | Aboul-Hosn et al. |
| 6,395,026 B1 | | 5/2002 | Aboul-Hosn et al. |
| 2003/0023201 A1 | | 1/2003 | Aboul-Hosn et al. |

FOREIGN PATENT DOCUMENTS

| | | |
|---|---|---|
| WO | WO 99/65546 | 12/1999 |
| WO | WO 00/12148 | 3/2000 |
| WO | WO 00/18448 | 4/2000 |
| WO | WO 00/19097 | 4/2000 |
| WO | WO 00/69489 | 11/2000 |

* cited by examiner

Primary Examiner—Jeffrey R. Jastrzab
(74) Attorney, Agent, or Firm—Ryan Kromholz & Manion, S.C.

(57) ABSTRACT

A cannulation system for cardiac support uses an inner cannula disposed within an outer cannula. The outer cannula includes a fluid inlet for placement within the right atrium of a heart. The inner cannula includes a fluid inlet extending through the fluid inlet of the outer cannula and the atrial septum for placement within at least one of the left atrium and left ventricle of the heart. The cannulation system also employs a pumping assembly coupled to the inner and outer cannulas to withdraw blood from the right atrium for delivery to the pulmonary artery to provide right heart support, or to withdraw blood from at least one of the left atrium and left ventricle for delivery into the aorta to provide left heart support, or both.

21 Claims, 14 Drawing Sheets

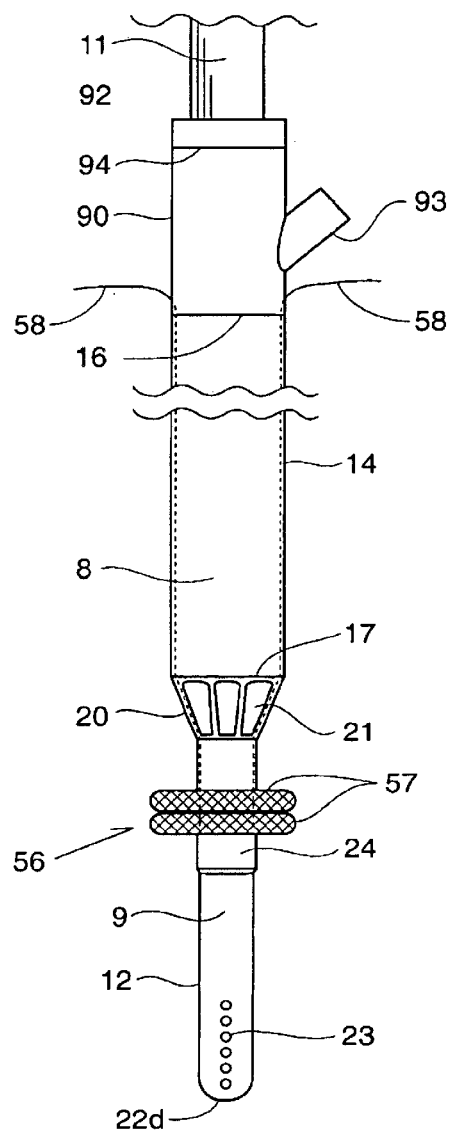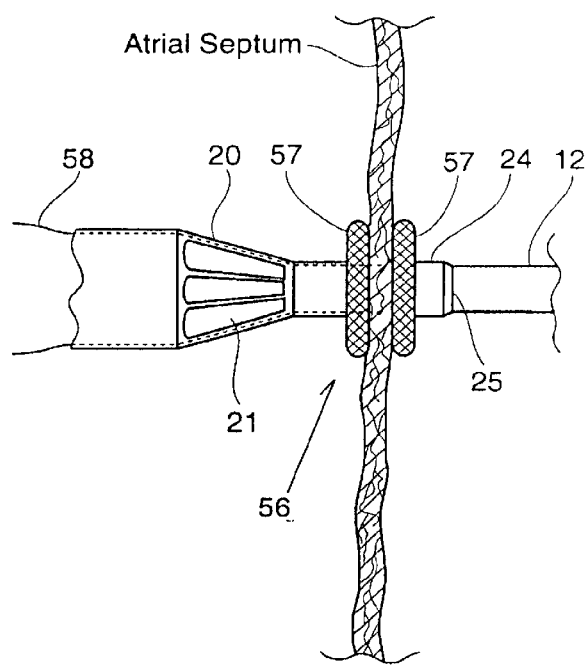
Fig. 7
Fig. 8

LEFT AND RIGHT SIDE HEART SUPPORT

REFERENCE TO RELATED APPLICATIONS

This application claims the benefit of U.S. Provisional Application No. 60/113,771, filed Dec. 23, 1998.

BACKGROUND OF THE INVENTION

I. Field of the Invention

The invention relates generally to the field circulatory support and, more specifically, to cannulas and related methods for use in cardiopulmonary bypass circuits and cardiopulmonary bypass graft procedures.

II. Discussion of the Prior Art

To perform bypass or grafting operations, many times the heart is stopped or significantly slowed by infusing chemicals (such as cardioplegia) into the patient's heart muscle or lowering the temperature of the heart. Additionally, the contractions of the patient's heart may be controlled utilizing other available technology, such as pacing electrodes. Prior to slowing or stopping the heart, the patient is placed on a cardiopulmonary bypass (CPB) circuit. Blood is withdrawn from the patient's heart, passed through a CPB circuit (generally comprising a blood pump, oxygenator, heat exchanger, and a blood filter) before being returned to the patient through a cannula which may be placed within the aorta. The cannulas that are placed within the patient generally range in size from 12 Fr. to 51 Fr., are generally tubular in shape, and may be reinforced with wire. Generally speaking, the cannula must be sufficiently small to permit insertion into the heart with minimal damage to the tissue, though it must be large enough to provide sufficient blood flow. In prior art systems where a blood pump is used to replace or assist the function of the heart, blood must be removed from the patient's vascular system, passed through a pump and returned to the patient's body through a second cannula.

Present bypass techniques require many feet of flexible tubing to connect the components in which the blood must flow through. Having the blood in contact with such a large amount of foreign material requires that the blood be treated with a large volume of Heparin to prevent clotting. Also, the large priming volume causes the patient's blood to be diluted with a large amount of saline. This serves to thin the patient's blood and lowers the oxygenation abilities, white blood cell count and increases the blood clotting time. While this type of bypass circuit works well, it is nonetheless complicated and requires a considerable amount of setup time and must be managed and constantly monitored by a skilled technician.

Another drawback with the prior art is that, if the surgeon desires to support both the right and left side of the heart (bi-ventricular support) independently without the use of an extracorporeal oxygenator, up to four cannulas need to be placed within the patient's circulatory system. With the addition of each cannula, further complications may arise. Placing multiple cannulas within the surgical field can cause clutter, thereby blocking access required to perform certain surgical procedures. Another danger associated with bi-ventricle support circuits is the possible formation of emboli in the patient's blood stream. If sufficiently high suction exists in the left atrium, air may be drawn from outside the heart through the insertion incision thereby forming an air emboli.

Presently there is a trend in the surgical arts toward performing beating heart surgery. In beating heart surgery, the patient's heart is slowed but not stopped. While performing beating heart coronary artery bypass graft (CABG), the oxygenator may be eliminated from the CPB circuit and the patient's lungs used to oxygenate the blood. Beating heart CABG has a number of advantages over stopped heart or full CPB CAEG. Specific studies have shown that patients placed on full bypass experience neurological problems, including but not limited to: memory loss, speech impairment, impaired coordination, systemic inflammatory response, and other complications. Also, many patients are too weak and/or infirm to survive the physical stresses associated with full CPB CABG, particularly patients of advanced age.

Due to the recency of beating heart surgery, specific cannulation systems have not been developed for use in procedures such as beating heart CABG. The present invention addresses this void in the prior art.

SUMMARY OF THE PRESENT INVENTION

The present invention relates to systems and methods for providing full or supplemental support for the heart during cardiac surgery. More specifically, the present invention provides simultaneous independent support of both the right and left side of the heart during cardiac surgery such as (but not necessarily limited to) beating heart CABG or still heart CABG.

One aspect of the invention provides a cannulation system for cardiac support. The system includes an inner cannula disposed within an outer cannula. The outer cannula includes a fluid inlet for placement within the right atrium of a heart. The inner cannula includes a fluid inlet extending through the fluid inlet of the outer cannula and the atrial septum for placement within at least one of the left atrium and left ventricle of the heart. The cannulation system also includes a pumping assembly coupled to the inner and outer cannulas to withdraw blood from the right atrium for delivery to the pulmonary artery to provide right heart support, or to withdraw blood from at least one of the left atrium and left ventricle for delivery into the aorta to provide left heart support, or both.

In a preferred embodiment, a cannula assembly and a pumping system cooperate to provide left and/or right heart support during cardiac surgery. The cannula assembly includes an inner cannula disposed generally coaxially within an outer cannula. To establish a bypass circuit with the present invention, the coaxial cannula assembly is introduced into the patient's heart through a single incision in the right atrium. The distal tip of the outer cannula is placed within the patient's right atrium. The inner cannula extends outwardly through an aperture formed in the distal end of the outer cannula and is passed through the atrial septum such that the distal end of the inner cannula is disposed within the patient's left atrium, or alternatively, within the patient's left ventricle. The pumping system includes a first blood pump connected to the proximal end of the outer cannula, and a second blood pump connected to the proximal end of the inner cannula. The first blood pump withdraws blood from the right atrium, which blood passes to the first blood pump through the annular flow path formed between the exterior surface of the inner cannula and the interior surface of the outer cannula. The outflow of the first blood pump is connected to an outflow cannula placed within the pulmonary artery, thereby providing right heart support. The second blood pump withdraws blood from the left atrium and/or left ventricle, which blood passes to the second blood pump through the flow path defined within the lumen of the inner cannula. The outflow of the second blood pump is connected to an outflow cannula placed within the aorta or any other major artery, thereby providing left heart support.

The cannula assembly of the present invention may be inserted either through an open chest cavity, such as when the patient's sternum is spread, or may be inserted during minimally invasive procedures where the cannula is placed within the patient's heart through access portals in the patient's chest. The associated methods of the present invention may also be used with a coaxial cannula, which consists of an inner and an outer cannula, that may be inserted through the patient's peripheral vasculature such as the jugular vein or femoral vein.

The cannulation system of the present invention provides independent drainage of the patient's left and right heart while minimizing the number of devices necessary to provide a bypass circuit. In a typical CPB circuit, many feet of flexible tubing are utilized to connect the bypass cannulas to the external support circuit, which typically consists of a blood pump, oxygenator and other components. As the patient's blood flows through the tubing, the blood is activated due to the contact with foreign materials, thereby activating the patient's immune system. Thus, after completion of the surgical procedure, the patient's immune system is further weakened due to the materials utilized during the procedure. The cannulation system of the present invention eliminates the oxygenator, blood filter, and the many feet of tubing typically found in a traditional CPB circuit. Eliminating the oxygenator and blood filter from the bypass circuit reduces hemolysis by minimizing the extent to which blood contacts foreign surfaces. Reducing the tubing serves to lower the priming volume of the bypass circuit, which in turn lessens the amount of saline introduced into the blood during priming operations. Minimizing the amount of saline added to the blood reduces the possibility that the patient will require a blood transfusion.

The cannulation system of the present invention is furthermore able to provide independent drainage of the patient's left and/or right heart through a single incision. In so doing, the cannulation system of the present invention reduces the possibility of air emboli forming within (or being introduced into) the patient's blood stream. In prior art cannulation arrangements, an incision must be made within the left atrium to receive a cannula coupled to a pump for withdrawing blood therefrom. If sufficient negative pressure develops within the left atrium, air may be drawn through the incision in the left atrium and form air emboli within the patient's blood stream. The cannulation system of the present invention positions the inner cannula within the left atrium by passing through the atrial septum, thereby eliminating the need for an incision in the outer wall of the left atrium. Therefore, to the extent sufficiently high negative pressures develop in the left atrium, the cannulation system of the present invention ensures that only non-oxygenated blood will be drawn through the atrial septum from the right atrium. In so doing, the present invention eliminates the possibility of air emboli forming in the patient's blood stream.

Utilizing the cannulation system of the present apparatus, a flow rate up to 6 liters per minute may be obtained with 100 mmHg outflow pressure and a rotational speed approximately between 2,000 and 50,000 rpm.

The coaxial cannula of the present invention may further include means for monitoring pressures within the patient's circulatory system. The cannula of the present invention can include devices such as pressure transducers and lumens disposed within the wall of the cannula. By incorporating sensing devices within the cannula of the present invention, further incisions and devices may be eliminated from the bypass circuit, thereby simplifying the circuit and reducing the overall cost of the procedure.

In an alternative embodiment, the cannula of the present invention may further contain a supplemental perfusion/drainage line for infusing cardioplegia into the heart or as a vent line for the heart.

In another embodiment of the present invention, any number of sensing devices may be employed to determine the location of the distal tip of the coaxial cannula within the patient's heart, including but not limited to a Doppler sensor, an ultrasound sensor, piezoelectric or silicone pressure sensor, and/or an oxygen saturation sensor.

In a still further embodiment of the present invention, the biventricular support system may further comprise a blood filter, a bubble trap, a means for oxygenating the patient's blood and a means for salvaging and re-infusing blood during the surgical procedure.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 7 is a side view of an alternate embodiment of the cannula assembly of the present invention wherein the outer cannula is equipped with a buckling cuff assembly;

FIG. 8 is a side view of the cannula assembly of FIG. 7 with the buckling cuff assembly deployed about either side of the atrial septum;

DETAILED DESCRIPTION OF THE PREFERRED EMBODIMENTS

Figure 1:
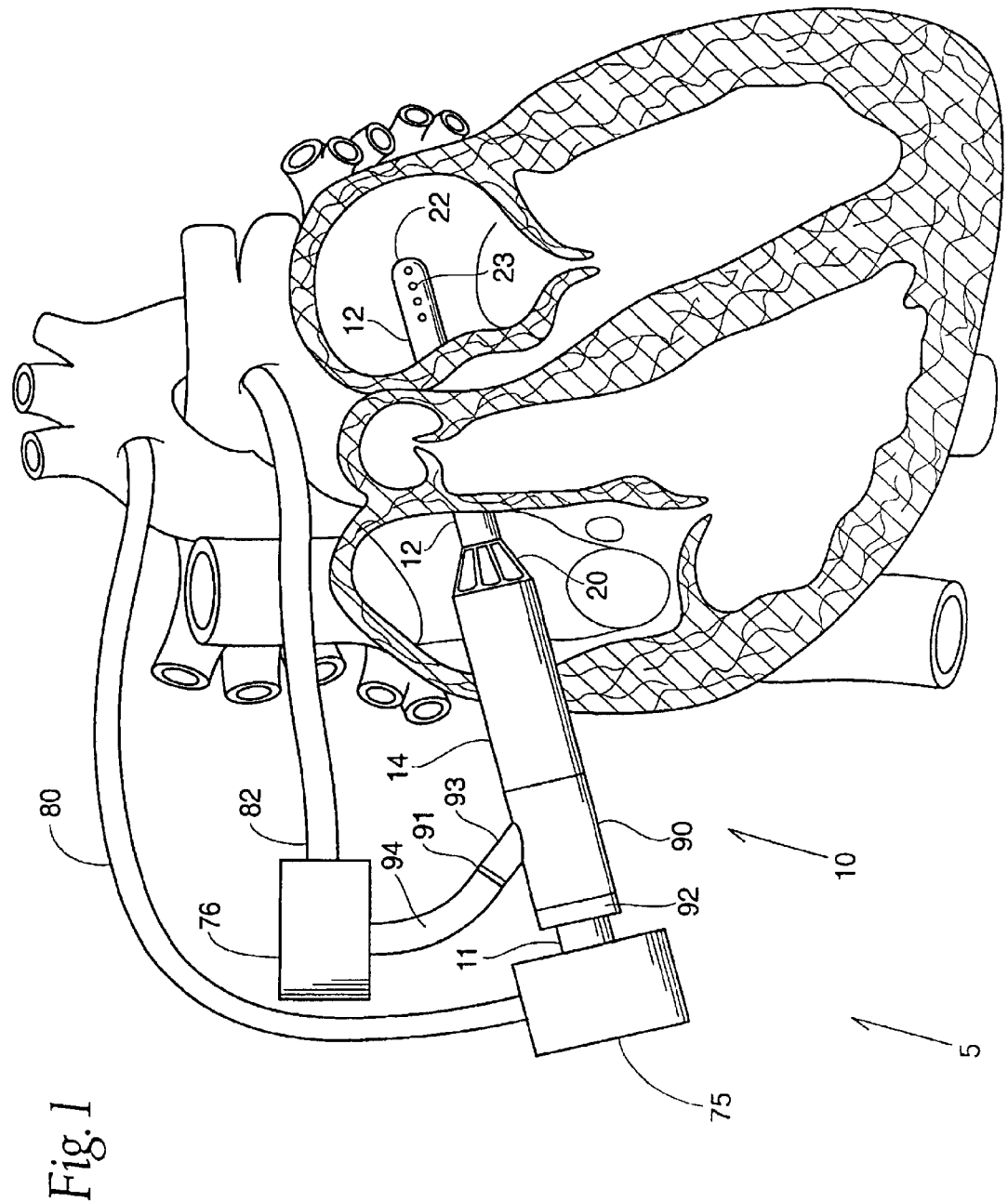
FIG. 1 is a schematic view of a cannulation system of the present invention in use with a human heart for providing right and/or left heart support during cardiac surgery.

The present invention involves a method and apparatus for providing full or supplemental support for the heart during cardiac surgery. Referring to FIG. 1, a cannulation system 5 according to one embodiment of the present invention is provided comprising a coaxial cannula assembly 10 having an outer cannula 14 extending into the right atrium of a patient's heart, and an inner cannula 12 disposed generally coaxailly within an outer cannula 14 and extending through the atrial septum into the left atrium.

As will be explained in greater detail below, the coaxial cannula assembly 10 has an inner flow path defined by the lumen within the inner cannula 12, and an outer flow path defined by the annular channel extending between the interior surface of the outer cannula 14 and the exterior surface of the inner cannula 12. The inner cannula 12 is communicatively coupled to a blood pump 75 such that oxygen-rich blood from the left atrium may be withdrawn via the inner flow path and rerouted into the aorta via an outflow cannula 80. The outer cannula 14 is communicatively coupled to a blood pump 76 such that oxygen-depleted blood from the right atrium may be withdrawn via the outer flow path and rerouted into the pulmonary artery via an outflow cannula 82. In this fashion, the cannulation system of the present invention is capable of providing full or partial support to both the right and left sides of the heart during heart surgery.

Figure 2:
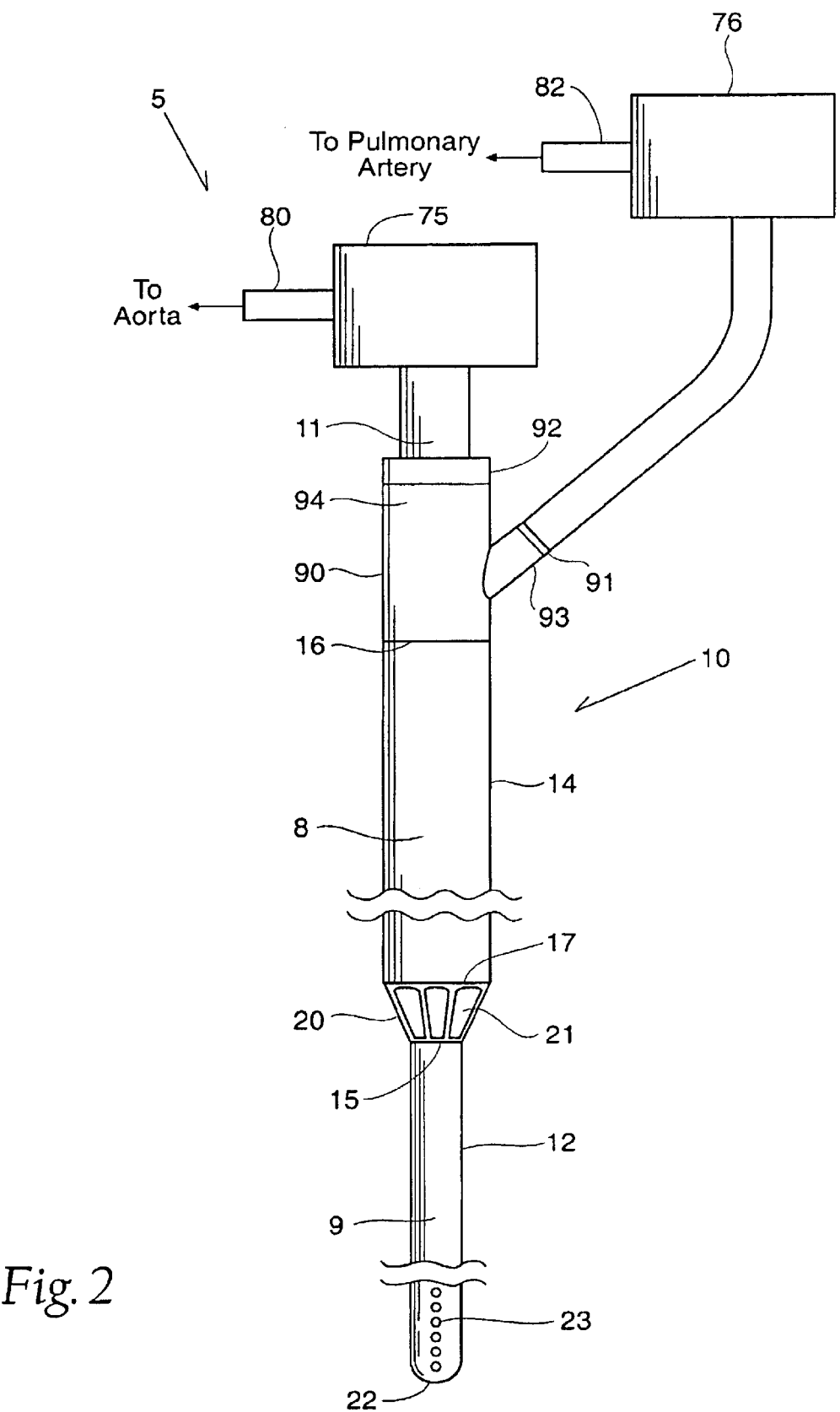
FIG. 2 is a side view of the cannulation system of FIG. 1, further illustrating the cannula assembly as including an inner cannula disposed within (and extending from) an outer cannula.

Referring to FIG. 2, the outer cannula 14 includes a generally cylindrical hollow body 8 extending between a proximal end 16 and a distal end 17, and a fluid inlet port 20 coupled to the distal end 17. The fluid inlet port 20 includes an aperture 15 at its distal end and plurality of apertures 21. The aperture 15 of fluid inlet port 20 permits the inner cannula 12 to extend past the distal end of the outer cannula 14 for insertion through the atrial septum and placement within the left side of the heart. The apertures 21 of fluid inlet port 20 permit the inflow of blood into the outer flow path formed between the exterior of the inner cannula 12 and the interior surface of the outer cannula 16 when the inner cannula 12 is disposed within the outer cannula 14. The inner cannula 12 includes a hollow body portion 9 extending between a proximal tip 11 and a distal tip 22. The distal tip 22 and proximal tip 11 each contain an aperture to permit fluid flow through the lumen extending therebetween. The proximal tip 11 of inner cannula 12 is coupled to the blood pump 75. The distal tip 22 of inner cannula 12 is adapted to be passed through the outer cannula 14, through the patient's atrial septum, and into position within the left atrium and/or left ventricle. A plurality of supplemental fluid inlet apertures 23 may be provided near the distal tip 22 of the inner cannula 12 to facilitate the inflow of blood from the left side of the heart into to the pump 75.

The cannula assembly 10 of the present invention may be formed of materials ranging from rigid to flexible. These materials may be silicone rubber or a similar material, although preferably the cannula assembly 10 will be constructed of a semi-rigid transparent material such as polyurethane or polyvinyl chloride. The inner and outer cannulas 12,14 of the present invention may contain a spiraling wire disposed within the cannula wall to reinforce the central portions thereof. Providing reinforcement in this manner facilitates easy handling and prevents the inner and outer cannulas 12, 14 from collapsing or being pinched shut, which may otherwise close off the flow of fluid to or from the patient. Other ways of reinforcing the tubular body of a cannula are known in the art and will adapt equally well to the present invention. In addition, no reinforcement may be needed if the tube material is sufficiently strong or if sufficient positive pressure is present within each cannula 12, 14. The distal tips of each cannula 12,14 are preferably designed so that they do not cause damage to the surrounding tissue when inserted into the patient. The cannulas 12, 14 may be formed either by extrusion, or a layering process whereby successive layers of materials are deposited on a mandrel until a desired wall thickness is achieved. Additionally, as will be discussed below, one or more lumens may be formed within the wall of the cannulas 12, 14 during construction to, for example, house sensing devices such as blood pressure sensors, oxygenation sensors, etc.

Figure 3:
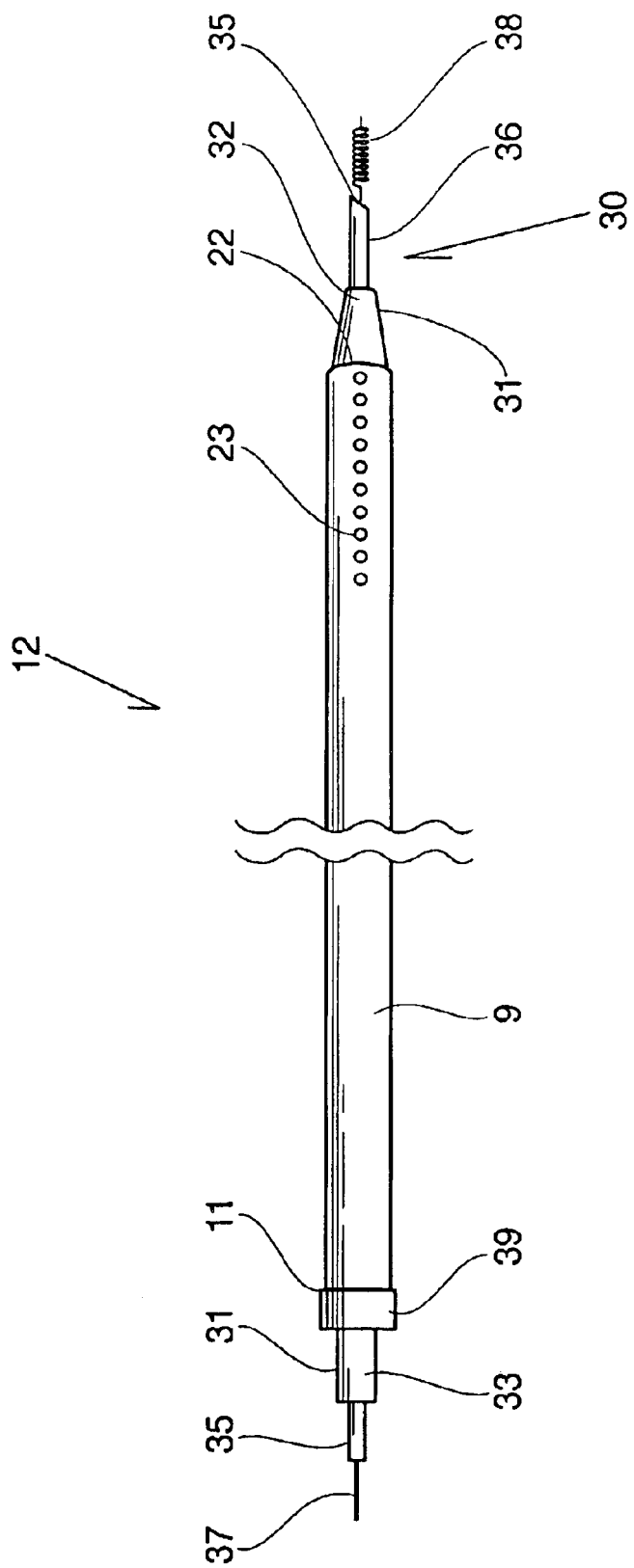
FIG. 3 is a side view of the inner cannula of FIGS. 1 and 2 equipped with a dilator assembly for facilitating passage of the inner cannula through the atrial septum according to the present invention.

Referring to FIG. 3, the step of passing the inner cannula 12 through the atrial septum may be accomplished through the use of a dilator assembly 30. Dilator assembly 30 includes a dilator 31, a needle 35 disposed within a lumen formed within the dilator 31, and a guide wire 37 disposed within a lumen formed within the needle 35. The dilator 31 has a distal tip 32 and a proximal tip 33 and a lumen extending therebetween. The dilator 31 is disposed through the main lumen of inner cannula 12. Distal tip 32 of dilator 30 protrudes beyond distal tip 22 of inner cannula 12. Distal tip 36 of needle 35 protrudes beyond distal tip 32 of dilator 31. The distal tips 32, 36, 38 of each component of the dilator assembly 30 are designed with sufficient rigidity and/or sharpness such that, alone or in combination, they provide the ability to pierce the atrial septum to facilitate passage of the inner cannula 12 therethrough. A hemostasis valve 39 may be provided at the proximal end 11 of inner cannula 12 in an effort to minimize or prevent blood flow out of (or air flow into) the heart during the process of passing the dilator assembly 30 through the inner cannula 12. It is to readily understood that the dilator assembly 30 is well known in the art and set forth by way of example only. Any number of additional commercially available dilator devices or assemblies can be employed to facilitate passing the distal tip 22 of the inner cannula 12 through the atrial septum for placement in the left side of the heart.

The method of inserting the cannula assembly 10 into the patient using the dilator assembly 30 will now be described with reference to FIGS. 1 and 3. The outer cannula 14 is first inserted into the patient's right atrium through an incision.

After inserting outer cannula 14 into the right atrium, the inner cannula 12 is prepared for insertion by introducing the dilator assembly 30 and guidewire 37 through the main lumen of the inner cannula 12. This forms the inner cannula assembly shown in FIG. 3. The inner cannula assembly is then advanced through hemostasis valve 92, distally through the main lumen of the outer cannula 14, and out the exit aperture formed in the fluid inlet port 20. The inner cannula assembly is then advanced through the right atrium until the needle 35 pierces the atrial septum. In this fashion, a user may then advance the entire dilator assembly 30 through the patient's atrial septum. Dilator 31 expands the opening in the atrial septum to a sufficient diameter to allow the inner cannula 12 to pass through therethrough. After placing the distal tip 22 of the inner cannula 12 within the left atrium, the dilator assembly 30 may be withdrawn from the main lumen of inner cannula 12.

As shown in FIGS. 1 and 2, the inner cannula 12 and outer cannula 14 are coupled to the pumps 75, 76 through the use of a Y-connector 90. The Y-connector 90 is a generally cylindrical tubular member having a hemostasis valve 92 at its proximal end and coupled to the outer cannula 14 at its distal end. The Y-connector 90 has a main lumen through which the proximal end 11 of the inner cannula 12 extends for passage through the hemostasis valve 92 and connection to the pump 75. Under the direction of the pump 75, oxygen-rich blood from the left side of the heart may be withdrawn through the inner flow path (within the inner cannula 12), passed through the hemostasis valve 92 to the pump 75, and passed through the outflow cannula 80 for deposit into the aorta. The Y-connector 90 also includes a secondary lumen extending within a port 93 extending angularly from the main body of the Y-connector 90. The port 93 is connected to the pump 76 through the use of a coupler 91 and conduit 94. Under the direction of the pump 76, oxygen-depleted blood from the right atrium may be withdrawn through the outer flow path (between the outer cannula 14 and inner cannula 12), passed through the port 93 to pump 76, and passed through the outflow cannula 82 for delivery into the pulmonary artery.

It is to readily understood that the Y-connector 90 is well known in the art and set forth by way of example only. Any number of additional commercially available coupling devices or assemblies can be employed without departing from the scope of the present invention. Y-connector 90 is preferably constructed of a clear rigid material, preferably a polycarbonate material, although Y-connector 90 may be constructed of any other clear or opaque rigid or semi-rigid biocompatible material. It is to be understood that the individual components shown associated with the Y-connector 90 (i.e. coupler 91 and hemostasis valve 92) are well known in the art and may comprise any number of similar commercially available devices without departing from the scope of the invention. For example, coupler 91 may comprise any well known and/or commercially available connecting barb or quick disconnect coupler. The hemostasis 92 may also comprise the proprietary hemostasis valves disclosed in co-pending and commonly assigned U.S. patent application Ser. No. 09/163,103 (filed Sep. 29, 1998 and entitled "Hemostasis Valve with Membranes Having Offset Apertures") and/or U.S. patent application Ser. No. 09/163,102 (filed Sep. 30, 1998 and entitled "Hemostasis Valve With Self-Sealing Flap"), both of which are hereby expressly incorporated herein by reference in their entirety. Outflow cannulas 80, 82 may comprise any number of commercially available conduits. As will be shown and described in greater detail below, outflow cannulas 80, 82 may also be equipped with at least one balloon disposed radially about the outer surface of the each outflow cannula 80, 82. In this fashion, once inserted within the patient's aorta and pulmonary artery, the balloons may be inflated to occlude the aorta and pulmonary artery to prevent blood from flowing retrograde into the patient's heart.

The pumps 75, 76 may comprise any number of pumping arrangements capable of providing full or partial support to the right and/or left heart during cardiac surgery. Such pumping arrangements can include, but are not necessarily limited to, any number of centrifugal pumps, axial pumps, and/or roller pumps that are well known in the art and commercially available, such as the 3M Sarns pump. Another pumping arrangement suited for use with the present invention is disclosed in co-pending and commonly assigned US patent application Ser. No. 09/166,135 (filed Sep. 30, 1998 and entitled "Blood Pump With Sterile Motor Casing"), the contents of which are hereby expressly incorporated herein by reference. The cannulation system of the present apparatus is capable of providing right and left heart support at flow rates up to 6 liters per minute with 100 mmHg outflow pressure and a rotational pump speed of approximately between 2,000 and 50,000 rpm.

Figure 4:
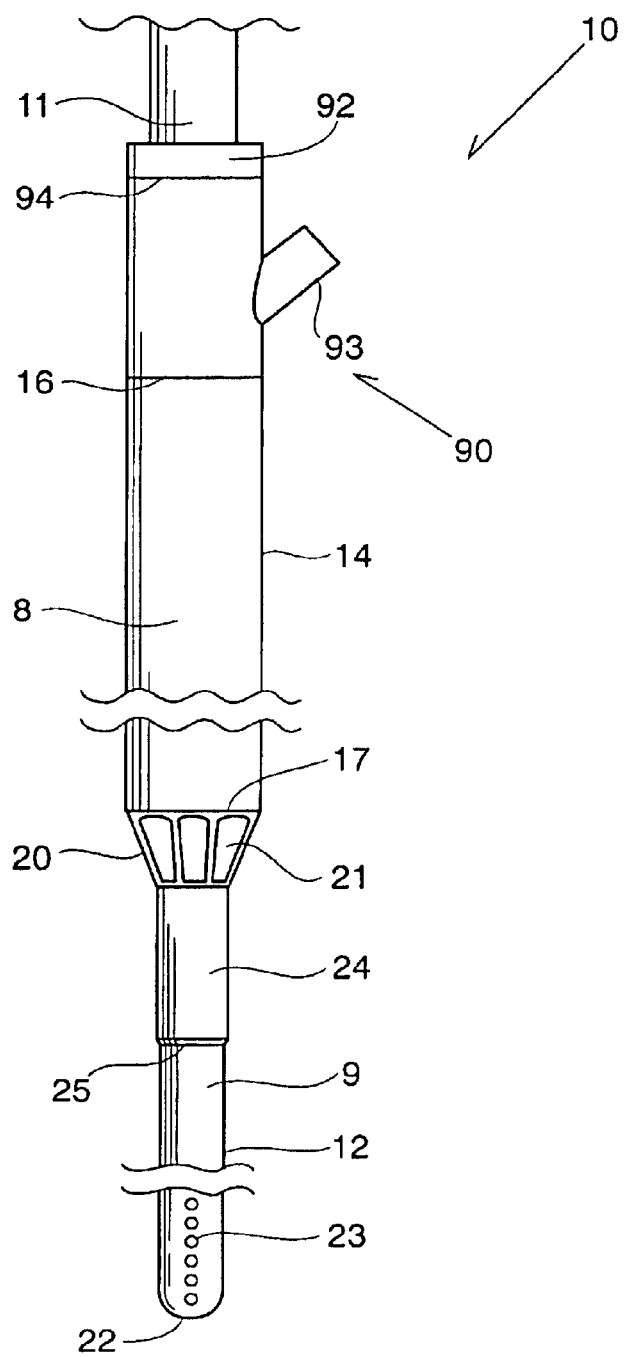
FIG. 4 is a side view of an alternate embodiment of the cannula assembly of the present invention wherein the outer cannula is equipped with a dilator tip to facilitate the introduction of the inner cannula into the left atrium.

FIG. 4 illustrates an alternate embodiment of the cannula assembly 10 of the present invention, wherein the outer cannula 14 is provided with a guiding dilator 24 extending distally from the fluid inlet port 20. The guiding dilator 24 comprises a tubular member having an interiorly disposed lumen and a distal tip 25 having an aperture through which the inner cannula 12 may be passed for insertion through the atrial septum and placement within the left side of the heart. Guiding dilator 24 is preferably formed of a sufficiently rigid material such as urethane, silicone, or polyvinyl chloride. Guiding dilator 24 is formed such that upon inserting the outer cannula 14 within the right atrium, the distal tip 25 of guiding dilator 24 is advanced through the atrium septum and disposed within the left atrium. Distal tip 25 of guiding dilator 24 is adapted to puncture and expand the atrial septum. Additionally, guiding dilator 24 is further adapted to guide the inner cannula 12, so that the distal tip 22 of inner cannula 12 may be easily placed within the left atrium or left ventricle. In this regard, guiding dilator 24 may contain a curved portion or be formed substantially straight as illustrated in FIG. 4. The outer cannula 14 is shown having the fluid inlet port 20 and guiding dilator 24 formed as a unitary article. Outer cannula 14 may be constructed in this fashion by carrying out the following steps: (1) selecting an appropriate sized mandrel; (2) pre-heating the mandrel to a selected temperature between about 100 and 300 degrees Celsius; (3) applying a layer of liquid material to the mandrel; (4) curing the first layer by applying heat; (5) disposing reinforcing wire about mandrel; (6) applying a second layer of material; and (7) curing the second layer of material by application of heat. It will be readily appreciated that, while shown as part of a unitary article in FIG. 4, it is within the scope of the present invention to provide the guiding dilator 24 and fluid inlet port 20 as separate elements coupled to the outer cannula 14.

Figure 5:
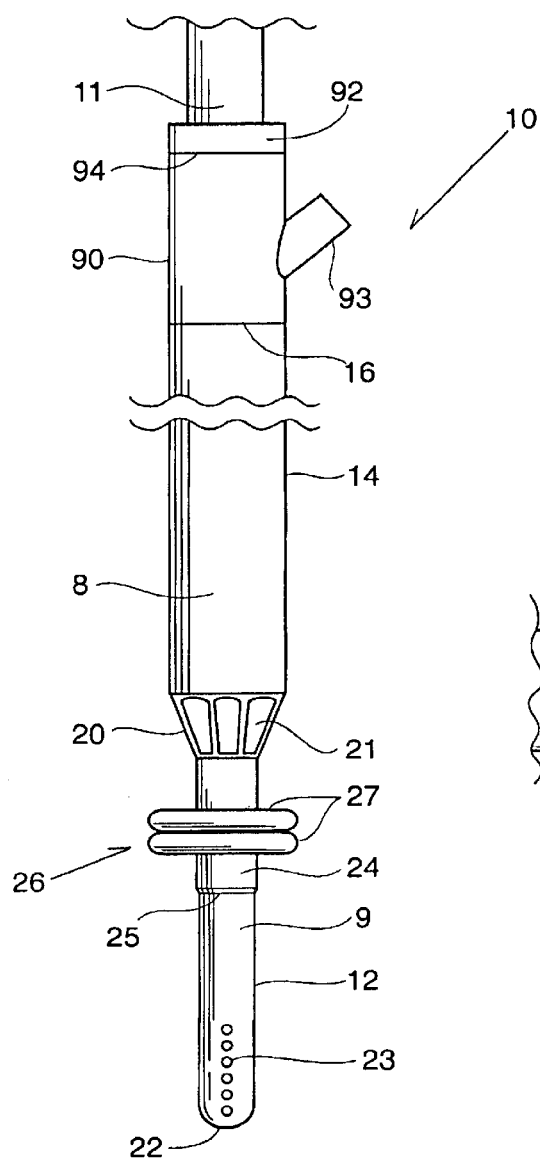
FIG. 5 is a side view of an alternate embodiment of the cannula assembly of the present invention wherein the outer cannula is equipped with an inflatable cuff assembly.
Figure 6:
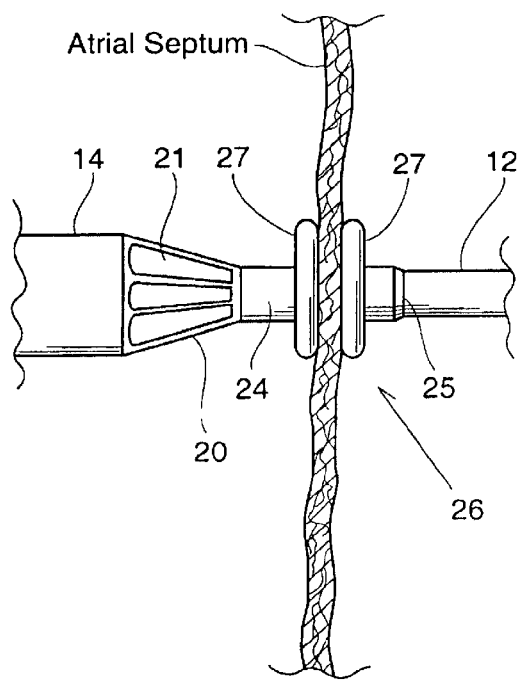
FIG. 6 is a side view of the cannula assembly of FIG. 5 with the inflatable cuff assembly deployed about either side of the atrial septum.

FIG. 5 illustrates an alternate embodiment of the cannula assembly 10 described above, wherein outer cannula 14 is further equipped with an inflatable cuff assembly 26. The inflatable cuff assembly 26 includes a pair of inflation members 27 (such as balloons) radially disposed about the guiding dilator 24. The inflation members 27 are coupled to a fluid source (not shown) and adapted to receive or sandwich the patient's tissue therebetween when inflated. FIG. 6 illustrates the inflatable cuff assembly 26 in use, with the individual inflation members 27 inflated and disposed on either side of the atrial septum. To accomplish this, the cannula assembly 10 is first introduced into the right atrium with the inflation members 27 in a fully deflated or low profile state. The outer cannula 14 is advanced within the right atrium until the distal tip 25 of the guiding dilator 24 pierces the atrial septum, allowing the placement of the inner cannula 12 within the left side of the heart. The guiding dilator 24 is preferably positioned such that the inflation members 27 are disposed on either side of the atrial septum. The inflation members 27 may thereafter be selectively inflated through the use of a fluid source (not shown) to secure a portion of the atrial septum therebetween. The inflatable cuff assembly 26 thereby provides a seal between the right atrium and the left atrium. Further still, the inflatable cuff assembly 26 serves to position and retain the cannula assembly 10 within the heart.

FIG. 7 illustrates an alternate embodiment of the cannula assembly 10 described above, wherein outer cannula 14 is further equipped with a bucking cuff assembly 56. The buckling cuff assembly 56 includes a length of fabric capable of having its ends or portions selectively drawn together to create a pair of cuff members 57 radially disposed about the guiding dilator 24. The step of drawing the ends or portions of the fabric together may be accomplished through the use of wires 58 disposed within lumens (not shown) formed in the wall of the outer cannula 14. It also may be possible to provide a slidable member (not shown) between the distal tip 25 of the guiding dilator 24 and the distal end of the fabric such that the slidable member can be drawn proximally towards the fluid inlet 20 to create the bucking cuffs 57. In either case, FIG. 8 illustrates the buckling cuff assembly 56 in use, with the individual cuff members 57 disposed on either side of the atrial septum. To accomplish this, the cannula assembly 10 is first introduced into the right atrium with the fabric extended in a low profile state such that the cuff members 57 are not formed. The outer cannula 14 is advanced within the right atrium until the distal tip 25 of the guiding dilator 24 pierces the atrial septum, allowing the placement of the inner cannula 12 within the left side of the heart. The guiding dilator 24 is preferably positioned such that the fabric extends on either side of the atrial septum. The cuff members 57 may thereafter be selectively formed by drawing the wires 58 to secure a portion of the atrial septum therebetween. The buckling cuff assembly 56 thereby provides a seal between the right atrium and the left atrium. The buckling cuff assembly 56 also serves to position and retain the cannula assembly 10 within the heart. As used herein, the term "fabric" refers to any structure produced by interlacing fibers. Such fibers include any threadlike material adapted for spinning or weaving. The fibers may be inorganic or organic. The fibers may also be constructed from any number of filaments or have a mono-filament construction. Suitable materials for the fabric can include polyester, polyethylene, nylon, polyefin, polypropylene, PTFE and polyurethane and silicone.

Figures 9, 10:
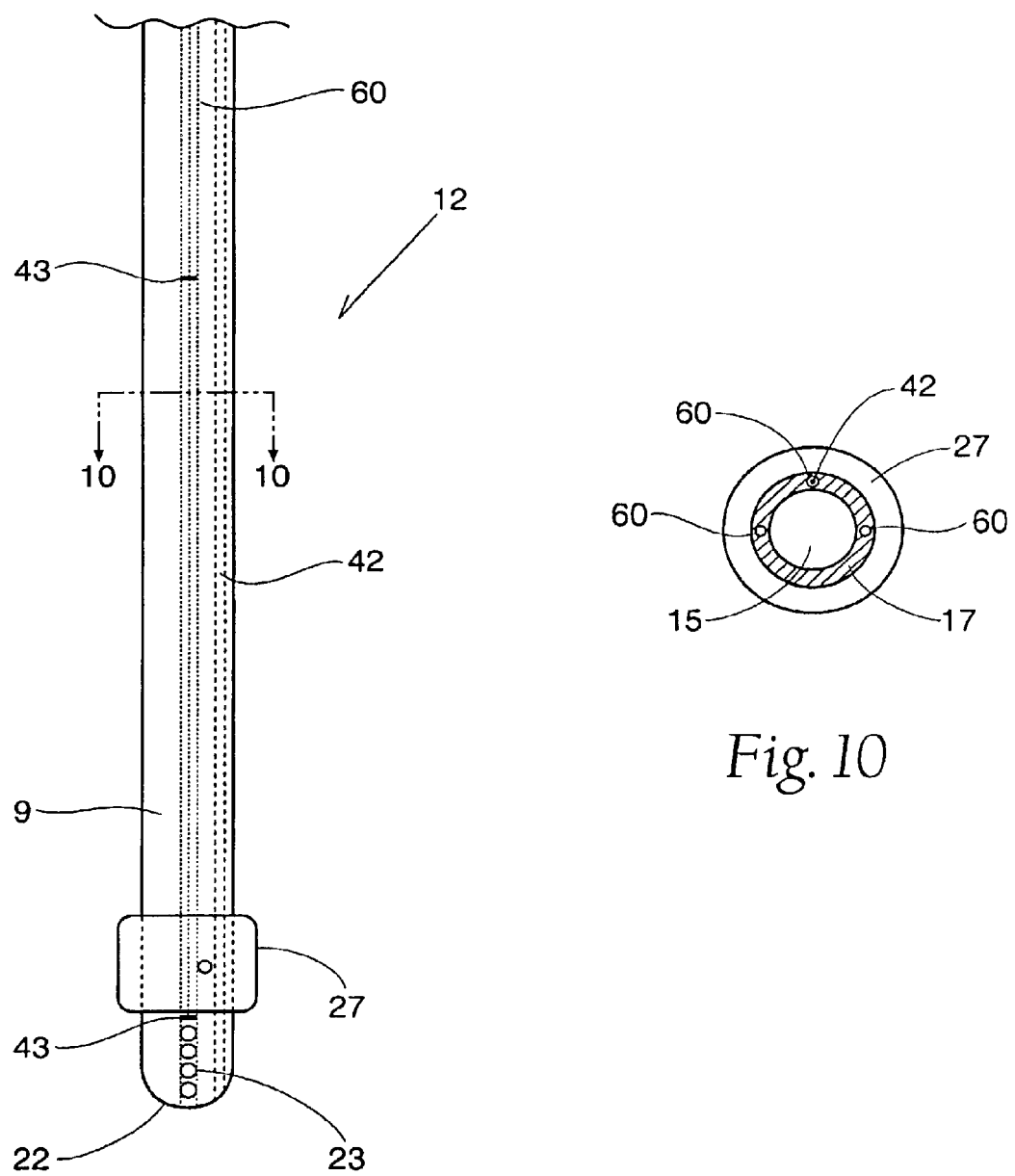
FIG. 9 is a side view of an alternate embodiment of the inner cannula of the present invention.
FIG. 10 is a cross sectional view of the inner cannula taken through lines 10—10 of FIG. 9.

FIGS. 9 and 10 illustrate an alternate embodiment of the inner cannula 12 equipped with a variety of additional features according to the present invention. In addition to the main lumen 15, the inner cannula 12 may be further equipped with one or more lumens 60 disposed within the side wall 17. Lumens 60 may be used for pressure measurements, injecting or withdrawing fluid, or for inflating balloon 27. Lumens 60 may also be used to receive a light guide, such as a fiber optic cable 42, for the purpose of projecting light from the distal end of the inner cannula 12. The illuminating tip of fiber optic cable 42 provides the user with direct or indirect visual reference that aids in placement of inner cannula 12. The lumens 60 of the inner cannula 12 are also suitable for receiving at least one pressure transducer 43. Pressure transducer 43 may be placed sufficiently close to the inner wall of inner cannula 12, thereby allowing the user to measure pressure and flow rate within inner cannula 12. Transducer 43 may be placed sufficiently close to the outer surface of inner cannula 12 to measure pressure and flow rate through outer cannula 14.

The inner cannula 12 may also be equipped with features for determining or tracking the location of the inner cannula 12 within the heart. For example, inner cannula 12 may further contain sensors (not shown) for determining oxygenation content within the patient's blood, such as saturated venous oxygen sensors. As distal tip 22 is advanced through the atrial septum into the left atrium, the oxygen content of the blood will increase, thereby signaling to the user that distal tip 22 is placed within the left atrium. Therefore, by measuring the oxygen content, the position of the distal tip 22 of cannula 12 may be readily determined. The inner cannula 12 may also be equipped with an ultrasound sensor disposed about or within the distal tip 22 of the inner cannula 12. When inserting inner cannula 12 into the heart, the user may determine placement of the distal tip 22 by monitoring the ultrasound sensor. As indicated by the sensor, areas of high flow will cause an alarm to sound, thereby alerting the user that the distal tip 22 may be improperly placed within a vessel or chamber of the heart. An example of such a use would be when advancing the inner cannula 12 toward the atrial septum, the ultrasound sensor will sound if the distal tip 22 is seated against the aorta instead of the atrial septum. In this fashion, a user will be provided a warning that a correction in alignment must be made. The ultrasound sensor may also be used to provide pressure measurements from the distal tip 22 of inner cannula 12 during insertion and after insertion. These pressure measurements may be utilized to determine the orientation of distal tip 22 with respect to the atrial septum.

Figure 12:
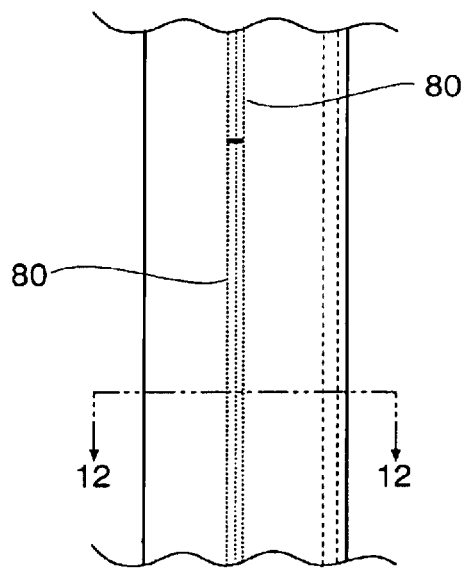
FIG. 12 is a cross sectional view of the inner cannula taken through lines 12—12 of FIG. 11.
Figure 12:
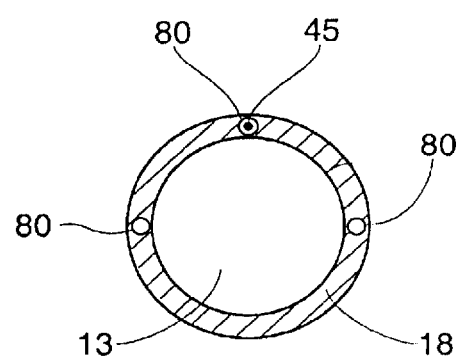
Figure 11:
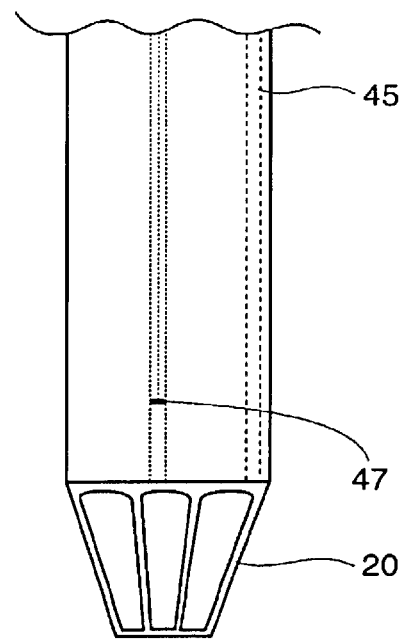
FIG. 11 is a side view of an alternate embodiment of the outer cannula of the present invention.

FIGS. 11 and 12 illustrate an alternate embodiment of the outer cannula 14 equipped with a variety of additional features according to the present invention. In addition to the main lumen 13, the outer cannula 14 may be further equipped with one or more lumens 80 disposed within the side wall 18. Lumens 80 may be used for pressure measurements, injecting or withdrawing fluid, or for inflating a balloon (not shown) disposed about the outer surface of cannula 14. Lumens 80 may also be used to receive a light guide, such as a fiber optic cable 45, for the purpose of projecting light from the distal end of the outer cannula 14. The illuminating tip of fiber optic cable 45 provides the user with direct or indirect visual reference that aids in placement of outer cannula 14. The lumens 80 of the outer cannula 14 are also suitable for receiving at least one pressure transducer 47. Pressure transducer 47 may be placed sufficiently close to the inner wall of the main lumen 13 of outer cannula 14, thereby allowing the user to measure pressure and flow rate within outer cannula 14. The pressure transducer 47 may also be placed sufficiently close to the outer surface of outer cannula 14 to measure pressure and flow rate around outer cannula 14.

The outer cannula 14 may also be equipped with features for determining or tracking the location of the outer cannula 14 within the heart. For example, the outer cannula 14 may be equipped with an ultrasound sensor disposed about or within the distal tip of the outer cannula 14. When inserting outer cannula 14 into the heart, the user may determine placement of the distal tip or fluid port 20 by monitoring the ultrasound sensor. High flow rate measurements will cause an alarm to sound. As such, a user may be alerted by the alarm when high flow rates are measured due to the distal tip or fluid port 20 being improperly placed within a vessel or chamber of the heart. The ultrasound sensor may also be used to provide pressure measurements from the distal tip or fluid port 20 of the outer cannula 14 during insertion and after insertion. These pressure measurements may be utilized to determine the orientation of the distal tip or fluid port 20 of the outer cannula 14 with respect to the atrial septum.

Figure 13:
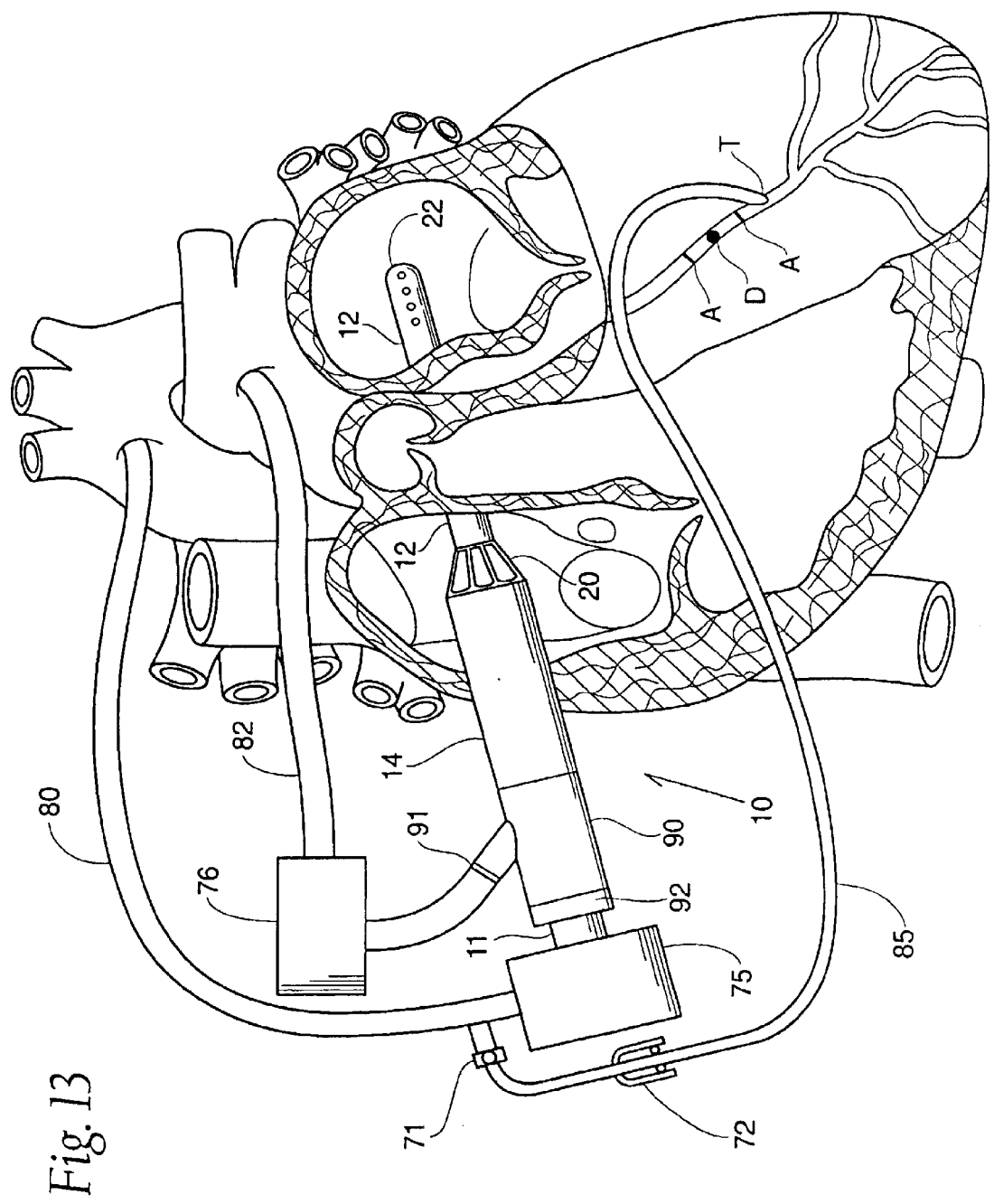
FIG. 13 is a schematic view of an alternate embodiment of the present invention wherein the cannulation system includes a supplemental perfusion conduit for delivering oxygen-rich blood from the left atrium to a target vessel (T) on the heart.

FIG. 13 illustrates an alternate embodiment of the cannulation system 5 of the present invention, wherein a supplemental perfusion conduit 85 is provided for perfusing a target vessel or artery (T) of the patient during surgical procedures. When performing an anastomosis, the surgeon typically occludes the target vessel (T) proximal to the arteriotomy (A). However, in so doing, this effectively cuts off the blood supply to the heart tissue downstream or distal to the occlusion (O) such that this tissue may not receive an adequate amount of oxygenated blood. As will be appreciated, this may cause damage to the tissue. In the embodiment shown, the supplemental perfusion conduit 85 is coupled to the outflow cannula 82 such that oxygen rich blood may be diverted into the target vessel (T) to perfuse the vessels distal to the arteriotomy (A). The supplemental perfusion conduit 85 may be provided with a stopcock 71 and flow regulator 72 disposed in-line to allow greater control over fluid flow rate through conduit 85 and/or to allow infusion of chemicals into the patient's circulatory system. Although not shown, it will be apparent to those skilled in the art that the supplemental perfusion arrangement discussed above may also be coupled to the outflow cannula 82 such that blood from the right atrium may be diverted for perfusing a target vessel or artery (T) of the patient during surgical procedures, albeit with blood having a lower oxygen content.

Figure 14:
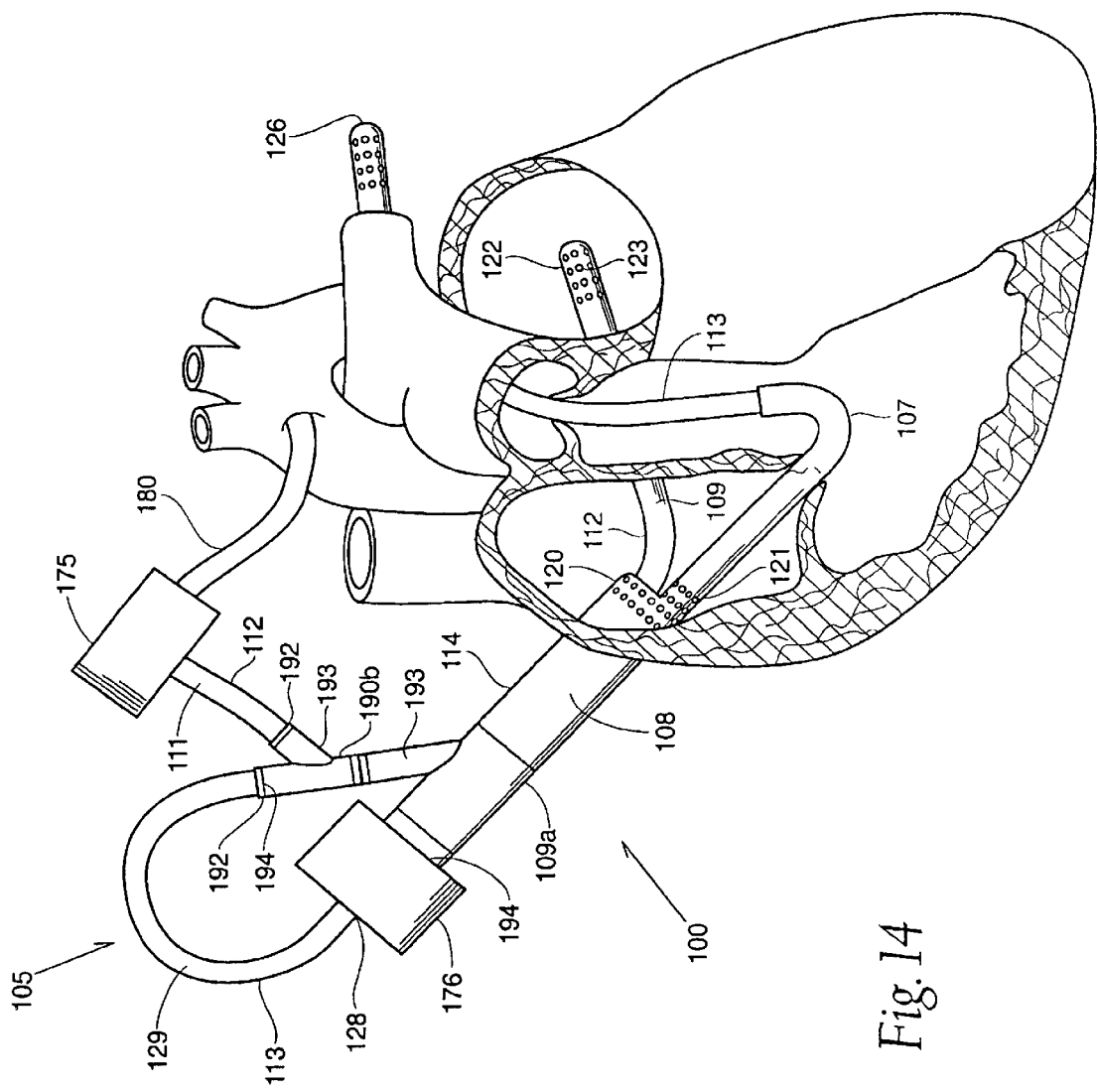
FIG. 14 is a schematic view of another cannulation system of the present invention in use with a human heart for providing right and/or left heart support during cardiac surgery.

FIG. 14 illustrates a cannulation system 105 according to an alternate embodiment of the present invention. The cannulation system 105 comprises a cannula assembly 100 having a variety of pumps and conduits coupled thereto for providing full or partial support to both the right and left sides of the heart during heart surgery. The cannula assembly 100 includes an outer cannula 114, an inner cannula 112, and an inner cannula 113. As will be explained in greater detail below, the inner cannula 112 cooperates with a pump 175 and an outflow cannula 180 to withdraw oxygen-rich blood from the left atrium for deposit in the aorta to thereby provide left heart support. The inner cannula 113 and outer cannula 114 cooperate with a pump 176 to withdraw oxygen-depleted blood from the right atrium for deposit in the pulmonary artery to thereby provide right heart support.

Figure 15:
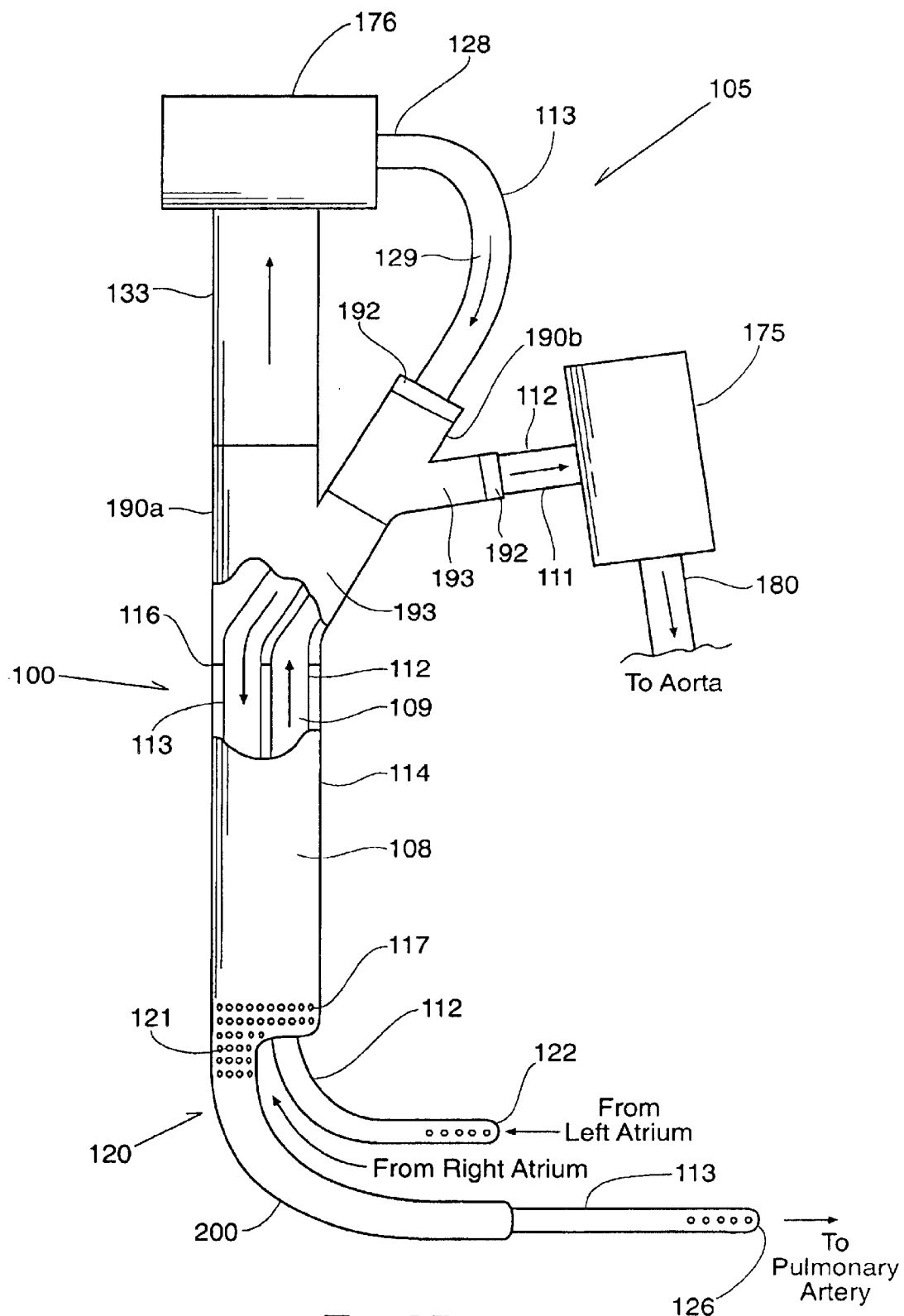
FIG. 15 is a side view of the cannulation system of FIG. 14, further illustrating the cannula assembly as including a pair of inner cannulas disposed within (and extending from) an outer cannula.
Figure 16:
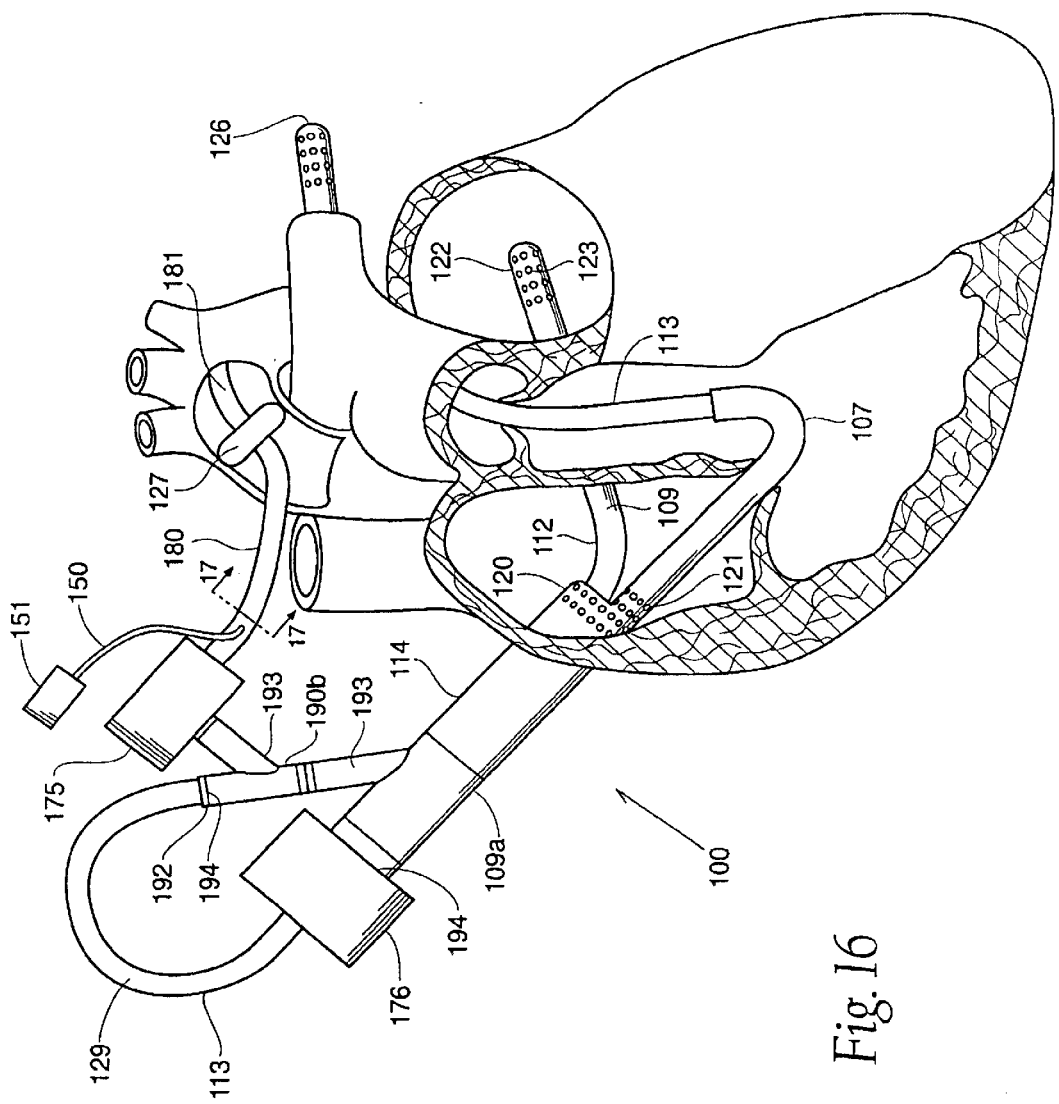
FIG. 16 is an alternate embodiment of the cannulation system shown in FIGS. 14 and 15, wherein an inflatable balloon is provided on the distal end of an outflow cannula 180 for selectively occluding the aorta.

With combined reference to FIGS. 15 and 16, the outer cannula 114 includes a main body portion 108 and a curved guiding portion 107 extending therefrom. The main body portion 108 includes a fluid inlet region 120 disposed within the right atrium having a plurality of apertures 121. The guiding portion 107 is a hollow and curved conduit extending from the fluid inlet region 120 of the main body portion 108 into the right ventricle. As can best be seen in FIG. 15, the guiding portion 107 has a curved or bent configuration that, when disposed within the right ventricle, directs the inner cannula 113 into the pulmonary artery. The inner cannula 112 has a distal end 122 extending through the atrial septum into the left atrium, a proximal end 111 coupled to the pump 175, and a mid-portion 109 extending therebetween which passes through the lumen of the outer cannula 114. Under the direction of the pump 175, oxygen-rich blood is withdrawn from the left atrium and transported through the inner cannula 112, the pump 175, and then through an outflow cannula 180 for deposit into the aorta. The inner cannula 113 has a distal end 126 extending into the pulmonary artery, a proximal end 128 coupled to the pump 175, and a mid-portion 129 extending therebetween which passes through the main lumen and curved guiding conduit 107 of the outer cannula 114. Under the direction of the pump 176, oxygen-depleted blood from the right atrium is withdrawn through the fluid inlet region 120 and transported through the outer cannula 114 (along the exterior surfaces of the inner cannulas 112, 113), the pump 176, and then through the inner cannula 113 for deposit in the pulmonary artery. A plurality of supplemental fluid inlet apertures 123 may be provided near the distal tip 122 of the inner cannula 112 to facilitate the inflow of blood from the left side of the heart into the pump 175. In similar fashion, a plurality of supplemental fluid inlet apertures 131 may be provided near the distal tip 126 of the inner cannula 113 to facilitate the outflow of blood into the right side of the heart from the pump 176.

A pair of Y-connectors 190a, 190b are provided, one (190a) coupled to the proximal end 116 of the outer cannula 114, and the other (190b) coupled to the port 193 of Y-connector 190a. The pump 176 may be coupled to Y-connector 190a via any number of conduits, such as tubular member 133. The proximal end 128 of inner cannula 113 is coupled to the pump 176. The mid-portion 129 of inner cannula 113 extends through the hemostasis valve 192 and main lumen of Y-connector 190b before passing through the lumens of Y-connector 190a, the main body portion 108, and the curved guiding portion 107 for passage into the pulmonary artery. The proximal end 111 of the inner cannula 112 is coupled to the inflow of pump 175. The mid-portion 109 of inner cannula 112 extends through the hemostasis valve 192 and lumens of Y-connector 190b before passing through the lumens of Y-connector 190a and the main body portion 108 for passage through the atrial septum and into the left atrium. Although not shown, it is to be readily understood that the cannulation system 105 can be equipped with a supplemental perfusion system as shown and described above with reference to FIG. 13, which perfusion system can be used with the coronary sinus for retrograde perfusion of coronaries.

Figure 17:
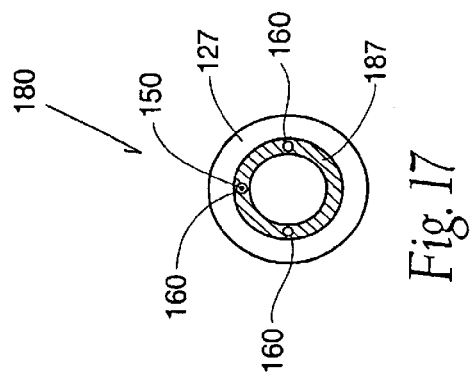
FIG. 17 is a cross sectional view of the outflow cannula 180 taken through lines 17—17 of FIG. 16.

FIGS. 16 and 17 illustrate an alternative embodiment of the cannulation system 105 of the present invention, wherein the outflow cannula 180 is provided with a balloon 127 disposed about the outer surface adjacent to distal tip 181 for the purpose of selectively occluding the aorta. The balloon 127 is coupled to a fluid source 151 capable of selectively inflating and deflating the balloon 127. The fluid source 151 is provided with a tube 150 which extends through a lumen 160 formed within the outflow cannula 180 for connection to the interior of the balloon 127. In one exemplary embodiment, the fluid source 151 may comprise a syringe which, when filled with saline or carbon dioxide, may be utilized to inflate or deflate balloon 127. Skilled artisans will appreciate that this is essentially the same as required for inflating and deflating the inflation members 27 discussed above with reference to FIGS. 9 and 10. The balloon 127 may be constructed from a resilient and flexible material, such as latex, silicone or urethane, sealed at its periphery against wall 182 of cannula 180. The sealing can be effected using heat bonding and/or any suitable adhesive. While deflated, the balloon 127 lies in a flush or low profile fashion against the surface of cannula 180. When inflated, the balloon 127 increases in size and surface area to occlude the patient's aorta.

Figure 18:
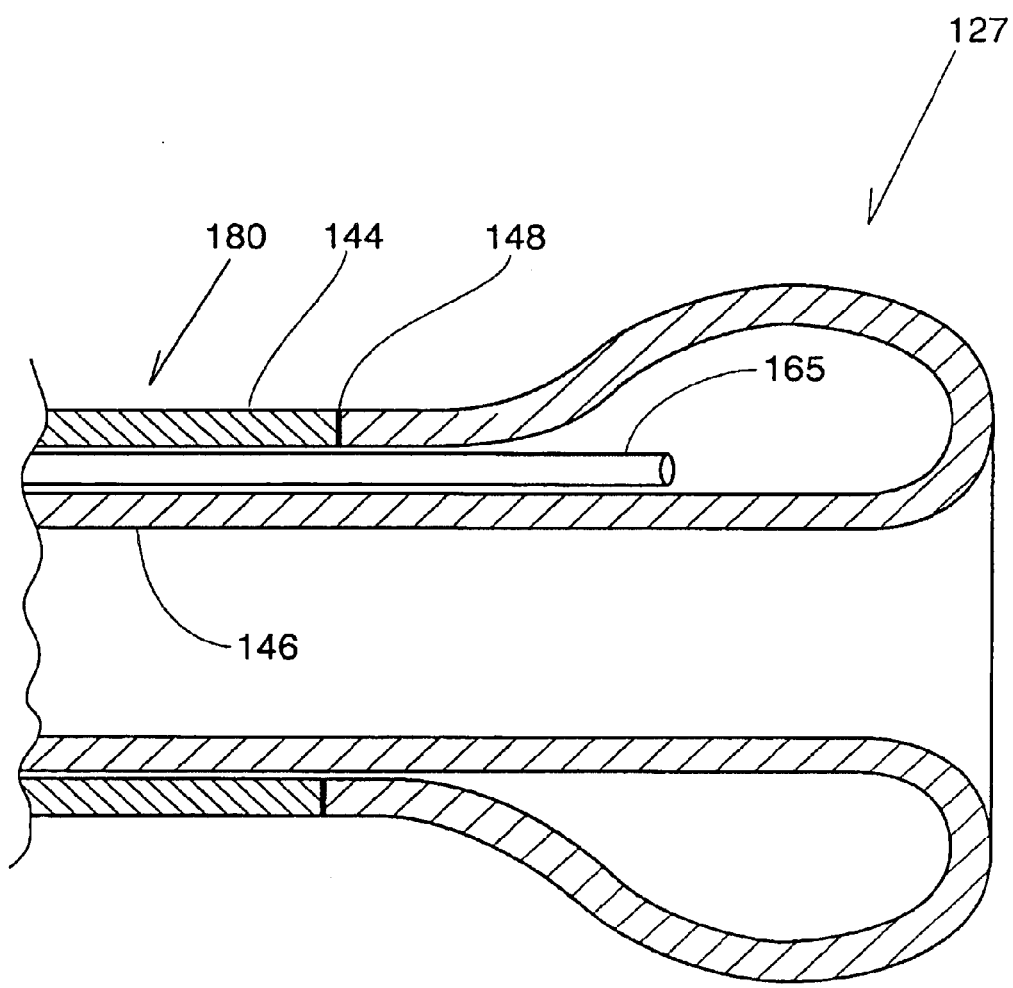
FIG. 18 is a partial sectional side view illustrating an alternative embodiment of forming the balloon on the distal tip of outflow cannula 180.

FIG. 18 illustrates an alternate construction for balloon 127, wherein the outflow cannula 180 has a layered construction with an inner wall portion 146 folded outward and sealed against an outer wall portion 144 to thereby form a fluid-tight continuous pocket comprising balloon 127. Portions 144 and 146 may be different materials, and they may be sealed together, by way of example, using heat bonding and/or adhesive at junction 148. As shown, supply tube 165 feeds into this pocket by passing between wall portions 144 and 146. However, this is not a strict requirement such that other ways of supplying balloon 127 with inflating material may be employed without departing from the scope of the present invention.

Figure 19:
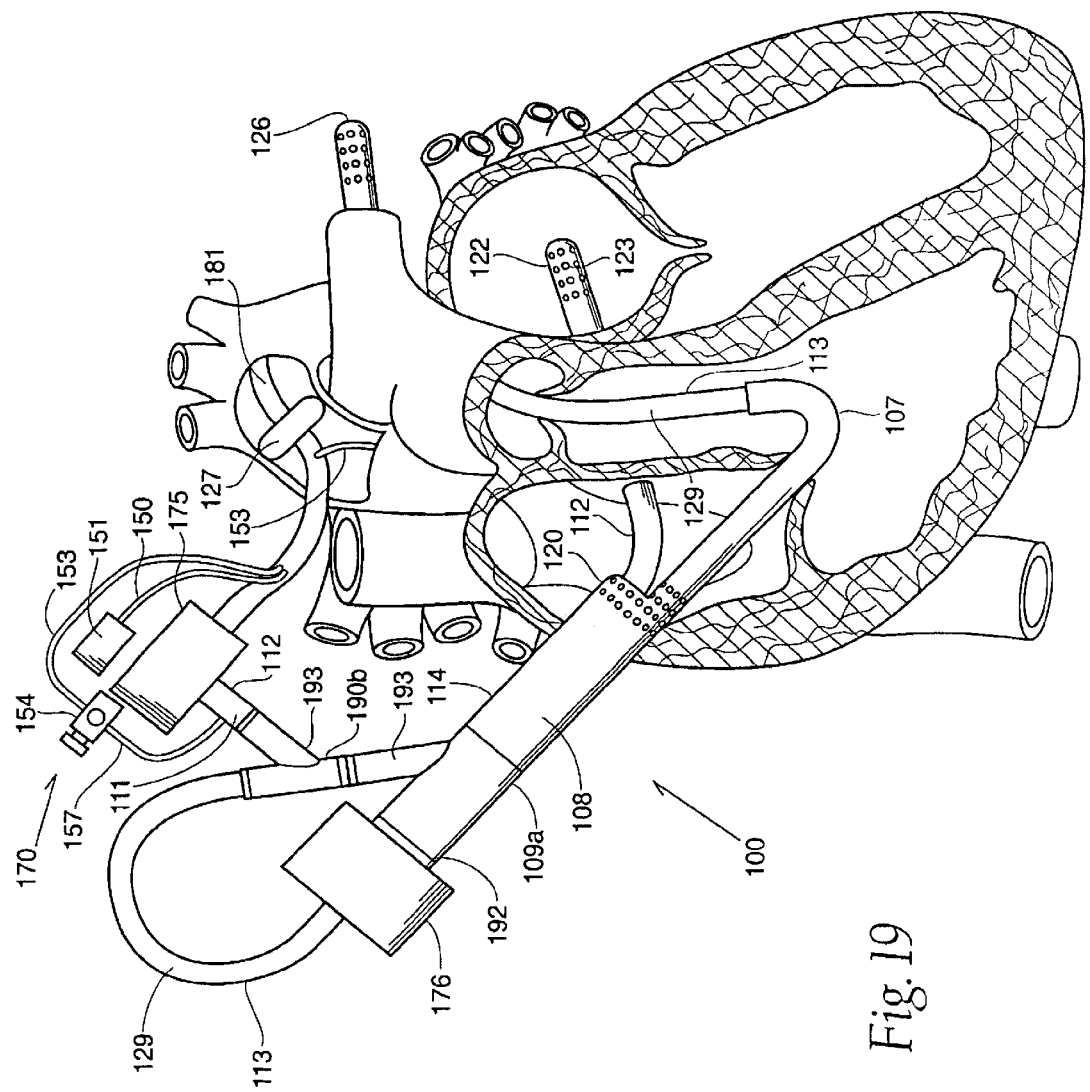
FIG. 19 is a schematic view of an alternate embodiment of the present invention wherein the cannulation system includes a system for infusing chemicals into the patient's heart or, alternatively, for withdrawing blood from the left ventricle.

FIG. 19 illustrates an alternate embodiment of the cannulation system 105 of the present invention, wherein a system 170 is provided for infusing chemical such as cardioplegia into the patient's heart or, alternatively, for withdrawing blood from the left ventricle. The system 170 includes a tube 153 which extend from a valve fitting 154, passes through a lumen formed within the outflow cannula 180 (such as lumen 160 of FIG. 17), and exits cannula 180 adjacent to balloon 127 for passage into the aorta. The valve fitting 154 may comprise a multi-position stopcock, which allows the user to select whether to employ the system 170 for infusing chemicals into, or withdrawing blood from, the aorta. When the system 170 is utilized for drainage, a second tube 157 is preferably provided coupling the valve fitting 154 to the inflow side of pump 175. The valve fitting 154 may then be employed to establish fluid communication between the pump 175 and the tube 153 such that blood may be withdrawn from the aorta under the direction of the pump 175. When utilized for chemical infusion, the valve fitting 154 may be coupled to a source of chemicals (such as a syringe having cardioplegia disposed therein) and employed to deliver the chemicals into the aorta.

Although not shown, any number of additional devices may be disposed within either or both bypass circuits. For example, a blood filter and/or heat exchanger may be disposed within the left heart bypass circuit by positioning these devices between the pump 75 and the aorta. Similarly, a blood filter and/or heat exchanger may be disposed within the right heart bypass circuit by positioning these devices between the pump 76 and the pulmonary artery.

The above are exemplary modes of carrying out the invention and are not intended to be limiting. It will be apparent to those skilled in the art that modifications thereto can be made without departing from the sprit and scope of the invention. Though the device and methods of the present invention are illustrated as being inserted directly into the heart, this does not preclude other methods of insertion, such as access through the femoral artery/vein and/or jugular vein/artery. It is also to be understood that, although the inner cannulas 12, 112 are shown with their distal tips 22, 122 extending into the left atrium, it is contemplated as part of the present invention that the inner cannula 12, 112 can be extended further into the left heart such that distal tips 22, 122 are disposed within the left atrium. It should also be recognized that, when utilizing the present invention for supporting the heart, the patient's heart may be stopped or significantly slowed by infusing drugs into the heart. Although described within the application as being of a coaxial embodiment, different geometrical embodiments are also contemplated. One such embodiment may be a dual lumen cannula having parallel cannulas.

What is claimed is:

1. A cannulation system for cardiac support comprising:
an inner cannula disposed within an outer cannula, the outer cannula including a fluid inlet sized and configured for placement within the right atrium of a heart, the inner cannula including a fluid inlet sized and configured to extend through the fluid inlet of the outer cannula and the atrial septum for placement within at least one of the left atrium and left ventricle of the heart; and
a pumping assembly coupled to the inner and outer cannulas and adapted to perform at least one of withdrawing blood from the right atrium for delivery to the pulmonary artery to provide right heart support, and withdrawing blood from at least one of the left atrium and left ventricle for delivery into the aorta to provide left heart support,
wherein the outer cannula is equipped with a dilator member extending distally from the fluid inlet of the outer cannula adapted to facilitate passing the fluid inlet of the inner cannula through the atrial septum for positioning within the left side of the heart;
wherein the pumping assembly includes a pump coupled to the inner cannula to withdraw blood from the left side of the heart, and an outflow cannula coupled to the pump and adapted to extend into the aorta for delivering the withdrawn blood into the aorta to provide left heart support.

2. A cannulation system for cardiac support comprising:
an inner cannula disposed within an outer cannula, the outer cannula including a fluid inlet sized and configured for placement within the right atrium of a heart, the inner cannula including a fluid inlet sized and configured to extend through the fluid inlet of the outer cannula and the atrial septum for placement within at least one of the left atrium and left ventricle of the heart; and
a pumping assembly coupled to the inner and outer cannulas and adapted to perform at least one of withdrawing blood from the right atrium for delivery to the pulmonary artery to provide right heart support, and withdrawing blood from at least one of the left atrium and left ventricle for delivery into the aorta to provide left heart support,
wherein the outer cannula is equipped with a dilator member extending distally from the fluid inlet of the outer cannula adapted to facilitate passing the fluid inlet of the inner cannula through the atrial septum for positioning within the left side of the heart, and
wherein the pumping assembly includes a pump coupled to the outer cannula adapted to withdraw blood from the right side of the heart, and an outflow cannula coupled to the pump and adapted to extend into the pulmonary artery for delivering the withdrawn blood into the pulmonary artery to provide right heart support.

3. The cannulation system of claim 1 or 2 and further, wherein the inner cannula is equipped with an inflation member near its distal end to facilitate positioning the fluid inlet of the inner cannula within the left side of the heart.

4. The cannulation system of claim 1 or 2 and further, wherein the inner cannula is equipped with at least one of an illumination system, a pressure sensing system, an oxygenation sensing system, and a flow rate sensing system.

5. The cannulation system of claim 1 or 2 and further, wherein the outer cannula is equipped with at least one of an illumination system, a pressure sensing system, an oxygenation sensing system, and a flow rate sensing system.

6. The cannulation system of claim 1 or 2 and further, wherein the dilator member of the outer cannula is equipped with an inflatable cuff assembly adapted for securing the dilator member in position through the atrial septum and sealing the aperture formed in the atrial septum by the dilator member.

7. The cannulation system of claim 6 and further, wherein the inflatable cuff assembly includes a first inflation member and a second inflation member which, in use, are adapted to be deployed on either side of the atrial septum.

8. The cannulation system of claim 7 and further, wherein the inflation members are selectively deployed through the use of a fluid source coupled to the interior of the inflation members.

9. The cannulation system of claim 8 and further, wherein the inner cannula is equipped with at least one lumen formed in the wall thereof to pass fluid from the fluid source to the interior of the inflation members to selectively inflate and deflate the inflation members.

10. The cannulation system of claim 1 or 2 and further, wherein the dilator member of the outer cannula is equipped with a bucking cuff assembly adapted for securing the dilator member in position through the atrial septum and for sealing the aperture formed in the atrial septum by the dilator member.

11. The cannulation system of claim 10 and further, wherein the bucking cuff assembly comprises a fabric material capable of being selectively drawn to form a first cuff portion and a second cuff portion which, in use, are adapted to be deployed on either side of the atrial septum.

12. The cannulation system of claim 11 and further, wherein the fabric material of the buckling cuff assembly is drawn to form the first and second cuff portions through the use of at least one wire extending within at least one lumen formed in the wall of the outer cannula.

13. The cannulation system of claim 1 or 2 and further, including a supplemental perfusion assembly for diverting blood from the heart to a target vessel on the heart.

14. The cannulation system of claim 13 and further, wherein the supplemental perfusion assembly includes a perfusion conduit communicatively coupled to the pumping system to divert a portion of the blood being withdrawn from one of the right and left side of the heart for delivery into the target vessel.

15. The cannulation system of claim 1 or 2 and further, wherein a fluid delivery system is provided for selectively transporting fluid other than blood into the aorta.

16. The cannulation system of claim 15 and further, wherein the fluid to be delivered into the aorta is cardioplegia.

17. A cannulation system for cardiac support comprising
an inner cannula disposed within an outer cannula, the outer cannula including a fluid inlet sized and configured for placement within the right atrium of a heart, the inner cannula including a fluid inlet sized and configured to extend through the fluid inlet of the outer cannula and the atrial septum for placement within at least one of the left atrium and left ventricle of the heart; and a pumping assembly coupled to the inner and outer cannulas and adapted to perform at least one of withdrawing blood from the right atrium for delivery to the pulmonary artery to provide right heart support, and withdrawing blood from at least one of the left atrium and left ventricle for delivery into the aorta to provide left heart support, wherein the pumping assembly includes a pump coupled to the inner cannula to withdraw blood from the left side of the heart, and an outflow cannula coupled to the pump and adapted to extend into the aorta for delivering the withdrawn blood into the aorta to provide left heart support, and wherein the outflow cannula from the pump is equipped with an inflation member near its distal end adapted to selectively occlude the aorta.

18. The cannulation system of claim 17 and further, wherein the inflation member is selectively deployed through the use of a fluid source coupled to the interior of the inflation member.

19. The cannulation system of claim 18 and further, wherein the outflow cannula from the pump is equipped with at least one lumen formed in the wall thereof to pass fluid from the fluid source to the interior of the inflation member to selectively inflate and deflate the inflation member.

20. A cannulation system for cardiac support comprising:
an inner cannula disposed within an outer cannula, the outer cannula including a fluid inlet sized and configured for placement within the right atrium of a heart, the inner cannula including a fluid inlet sized and configured to extend through the fluid inlet of the outer cannula and the atrial septum for placement within at least one of the left atrium and left ventricle of the heart; and a pumping assembly coupled to the inner and outer cannulas and adapted to perform at least one of withdrawing blood from the right atrium for delivery to the pulmonary artery to provide right heart support, and withdrawing blood from at least one of the left atrium and left ventricle for delivery into the aorta to provide left heart support;

wherein the pumping assembly includes a pump coupled to the outer cannula to withdraw blood from the right side of the heart, and an outflow cannula coupled to the pump and adapted to extend into the pulmonary artery for delivering the withdrawn blood into the pulmonary artery to provide right heart support; and wherein the outflow cannula coupled to the pump comprises a second inner cannula that is adapted to extend from the pump, through the outer cannula, and out the fluid inlet of the outer cannula such that a fluid outlet of the second inner cannula is disposed within the pulmonary artery.

21. The cannulation system of claim 20 and further, wherein the outer cannula includes a curved conduit extending distally from the fluid inlet through which the second inner cannula is adapted to pass in order to position the fluid outlet of the second inner cannula in the pulmonary artery.

* * * * *